(12) United States Patent
Baynham et al.

(10) Patent No.: US 7,711,420 B2
(45) Date of Patent: *May 4, 2010

(54) CLOSED-LOOP CONTROL OF CARDIOPROTECTIVE PRE-EXCITATION PACING

(75) Inventors: Tamara Colette Baynham, Piscataway, NJ (US); Quan Ni, Shoreview, MN (US); Shelley M. Cazares, Washington, DC (US); Kevin J. Stalsberg, White Bear Lake, MN (US); Yi Zhang, Blaine, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 235 days.

This patent is subject to a terminal disclaimer.

(21) Appl. No.: 11/687,957

(22) Filed: Mar. 19, 2007

(65) Prior Publication Data
US 2008/0234774 A1    Sep. 25, 2008

(51) Int. Cl.
A61N 1/00    (2006.01)
(52) U.S. Cl. .......................................................... 607/9
(58) Field of Classification Search .................... 607/3, 607/9; 600/16, 18
See application file for complete search history.

(56) References Cited

U.S. PATENT DOCUMENTS

| 7,295,874 | B2 | 11/2007 | Prinzen et al. |
| 7,450,988 | B2 * | 11/2008 | Ross et al. ....................... 607/9 |
| 2005/0065568 | A1 | 3/2005 | Liu et al. |
| 2006/0241704 | A1 | 10/2006 | Shuros et al. |
| 2006/0247702 | A1 | 11/2006 | Stegemann et al. |
| 2006/0259087 | A1 | 11/2006 | Baynham et al. |
| 2006/0259088 | A1 | 11/2006 | Pastore et al. |
| 2006/0287684 | A1 | 12/2006 | Baynham et al. |
| 2007/0150005 | A1 | 6/2007 | Sih et al. |
| 2007/0191892 | A1 * | 8/2007 | Mullen et al. ................... 607/9 |
| 2008/0004669 | A1 | 1/2008 | Sathaye et al. |

FOREIGN PATENT DOCUMENTS

| WO | WO-93/02745 A1 | 2/1993 |
| WO | WO-2004/024229 A1 | 3/2004 |
| WO | WO-2006/105474 A2 | 10/2006 |

OTHER PUBLICATIONS

"International Application No. PCT/US2008/003594, Written Opinion mailed Jul. 9, 2008", 6 pgs.
"International Application No. PCT/US2008/003594, International Search Report mailed Jul. 9, 2008", 5 pgs.

(Continued)

Primary Examiner—George Manuel
Assistant Examiner—Robert N Wieland
(74) Attorney, Agent, or Firm—Schwegman, Lundberg & Woessner, P.A.

(57) ABSTRACT

Cardioprotective pre-excitation pacing may be applied to stress or de-stress a particular myocardial region delivering of pacing pulses in a manner that causes a dyssynchronous contraction. Such dyssynchronous contractions are responsible for the desired cardioprotective effects of pre-excitation pacing but may also be hazardous. Described herein is a method and system that uses measures of ventricular dyssynchrony or a patient's physiological response to ventricular dyssynchrony to control the delivery of cardioprotective pre-excitation pacing in closed-loop fashion.

20 Claims, 5 Drawing Sheets

OTHER PUBLICATIONS

Ovize, M., et al., "Stretch preconditions canine myocardium.", *Am J Physiol.*, 266(1 Pt 2), (Jan. 1994), H137-H146.

Prinzen, F. W., "Mapping of Regional Myocardial Strain and Work During Ventricular Pacing: Experimental Study Using Magnetic Resonance Imaging Tagging", *Journal of the American College of Cardiology*, 33(6), (May, 1999), 1735-1742.

Prinzen, F. W., et al., "Relation between the pacing induced sequence of activation and left ventricular pump function in animals.", *Pacing Clin Electrophysiol.*, 25(4 Pt 1), (Apr. 2002), 484-498.

Vanagt, W. Y., et al., "Pacing-induced Dys-Synchrony Preconditions Rabbit Myocardium Against Ischemia/Reperfusion Injury.", *Circulation*, 114(1 Suppl), (Jul. 4, 2006), 1264-1269.

\* cited by examiner

CLOSED-LOOP CONTROL OF CARDIOPROTECTIVE PRE-EXCITATION PACING

FIELD OF THE INVENTION

This invention pertains to cardiac rhythm management devices such as pacemakers and other implantable devices.

BACKGROUND

Coronary artery disease (CAD) occurs when the coronary arteries that supply blood to the heart muscle become hardened and narrowed due to atherosclerosis. The arteries harden and become narrow due to the buildup of plaque on the inner walls or lining of the arteries. Blood flow to the heart is reduced as plaque narrows the coronary arteries. This decreases the oxygen supply to the heart muscle. A myocardial infarction (MI), or heart attack, occurs when atherosclerotic plaque within a coronary artery ruptures and leads to the clotting of blood (thrombosis) within the artery by exposing the highly thrombogenic lipid core of the plaque to the blood. The complete or nearly complete obstruction to coronary blood flow can damage a substantial area of heart tissue and cause sudden death, usually due to an abnormal heart rhythm that prevents effective pumping.

Besides causing an MI, CAD can also produce lesser degrees of cardiac ischemia due to the narrowing of a coronary artery lumen by atherosclerotic plaque. When blood flow and oxygen supply to the heart is reduced, patients often experience chest pain or discomfort, referred to as angina pectoris. Angina pectoris serves as a useful warning of insufficient myocardial perfusion which can lead to the more serious situation such as a heart attack or cardiac arrhythmia. Patients who experience anginal episodes are commonly treated either with medication or by surgical revascularization. It has also been found, however, that patients who experience anginal episodes prior to a heart attack often have a lower mortality rate than heart attack patients who do not experience such episodes. It is theorized that this phenomenon may be due to preconditioning of the heart by the anginal episodes which thereby renders the myocardial tissue less likely to become infarcted if blood supply is sharply reduced by a subsequent coronary thrombus.

Heart failure (HF) is a debilitating disease that refers to a clinical syndrome in which an abnormality of cardiac function causes a below normal cardiac output that can fall below a level adequate to meet the metabolic demand of peripheral tissues. Heart failure can be due to a variety of etiologies with ischemic heart disease being the most common. Inadequate pumping of blood into the arterial system by the heart is sometimes referred to as "forward failure," with "backward failure" referring to the resulting elevated pressures in the lungs and systemic veins which lead to congestion. Backward failure is the natural consequence of forward failure as blood in the pulmonary and venous systems fails to be pumped out. Forward failure can be caused by impaired contractility of the ventricles due, for example, to coronary artery disease, or by an increased afterload (i.e., the forces resisting ejection of blood) due to, for example, systemic hypertension or valvular dysfunction. One physiological compensatory mechanism that acts to increase cardiac output is due to backward failure which increases the diastolic filling pressure of the ventricles and thereby increases the preload (i.e., the degree to which the ventricles are stretched by the volume of blood in the ventricles at the end of diastole). An increase in preload causes an increase in stroke volume during systole, a phenomena known as the Frank-Starling principle. Thus, heart failure can be at least partially compensated by this mechanism but at the expense of possible pulmonary and/or systemic congestion.

When the ventricles are stretched due to the increased preload over a period of time, the ventricles become dilated. The enlargement of the ventricular volume causes increased ventricular wall stress at a given systolic pressure. Along with the increased pressure-volume work done by the ventricle, this acts as a stimulus for hypertrophy of the ventricular myocardium which leads to alterations in cellular structure, a process referred to as ventricular remodeling. Ventricular remodeling leads to further dysfunction by decreasing the compliance of the ventricles (thereby increasing diastolic filling pressure to result in even more congestion) and causing eventual wall thinning that causes further deterioration in cardiac function. It has been shown that the extent of ventricular remodeling is positively correlated with increased mortality in HF patients.

A myocardial infarction (MI) is the irreversible damage done to a segment of heart muscle by ischemia, where the myocardium is deprived of adequate oxygen and metabolite removal due to an interruption in blood supply. It is usually due to a sudden thrombotic occlusion of a coronary artery, commonly called a heart attack. If the coronary artery becomes completely occluded and there is poor collateral blood flow to the affected area, a transmural or full-wall thickness infarct can result in which much of the contractile function of the area is lost. Over a period of one to two months, the necrotic tissue heals, leaving a scar. The most extreme example of this is a ventricular aneurysm, where all of the muscle fibers in the area are destroyed and replaced by fibrous scar tissue. Even if the ventricular dysfunction as a result of the infarct is not immediately life-threatening, a common sequela of a transmural myocardial infarction, or any major MI, especially in the left ventricle, is heart failure brought about by ventricular remodeling in response to the hemodynamic effects of the infarct that causes changes in the shape and size of the ventricle. The remodeling is initiated in response to a redistribution of cardiac stress and strain caused by the impairment of contractile function in the infarcted area as well as in nearby and/or interspersed viable myocardial tissue with lessened contractility due to the infarct. Following an MI, the infarcted area includes tissue undergoing ischemic necrosis and is surrounded by normal myocardium. Until scar tissue forms and even after it forms, the area around the infarcted area is particularly vulnerable to the distending forces within the ventricle and undergoes expansion over a period of hours to days. Over the next few days and months after scar tissue has formed, global remodeling and chamber enlargement occur due to complex alterations in the architecture of the ventricle involving both infarcted and non-infarcted areas. It has been found that the extent of left ventricular remodeling in the late period after an infarction, as represented by measurements of end-systolic and end-diastolic left ventricular volumes, is an even more powerful predictor of subsequent mortality than the extent of coronary artery disease.

Remodeling is thought to be the result of a complex interplay of hemodynamic, neural, and hormonal factors that occur primarily in response to myocardial wall stress. As noted above, one physiological compensatory mechanism that acts to increase cardiac output is increased diastolic filling pressure of the ventricles as an increased volume of blood is left in the lungs and venous system, thus increasing preload. The ventricular dilation resulting from the increased preload causes increased ventricular wall stress at a given systolic pressure in accordance with Laplace's law. Along with the increased pressure-volume work done by the ventricle, this acts as a stimulus for compensatory hypertrophy of the ventricular myocardium. Hypertrophy can increase systolic pressures but, if the hypertrophy is not sufficient to meet the increased wall stress, further and progressive dilation results. This non-compensatory dilation causes wall thinning and further impairment in left ventricular function. It also has been shown that the sustained stresses causing hypertrophy may induce apoptosis (i.e., programmed cell death) of cardiac muscle cells. Thus, although ventricular dilation and hypertrophy may at first be compensatory and increase cardiac output, the process ultimately results in further deterioration and dysfunction.

DETAILED DESCRIPTION

Figure 1:
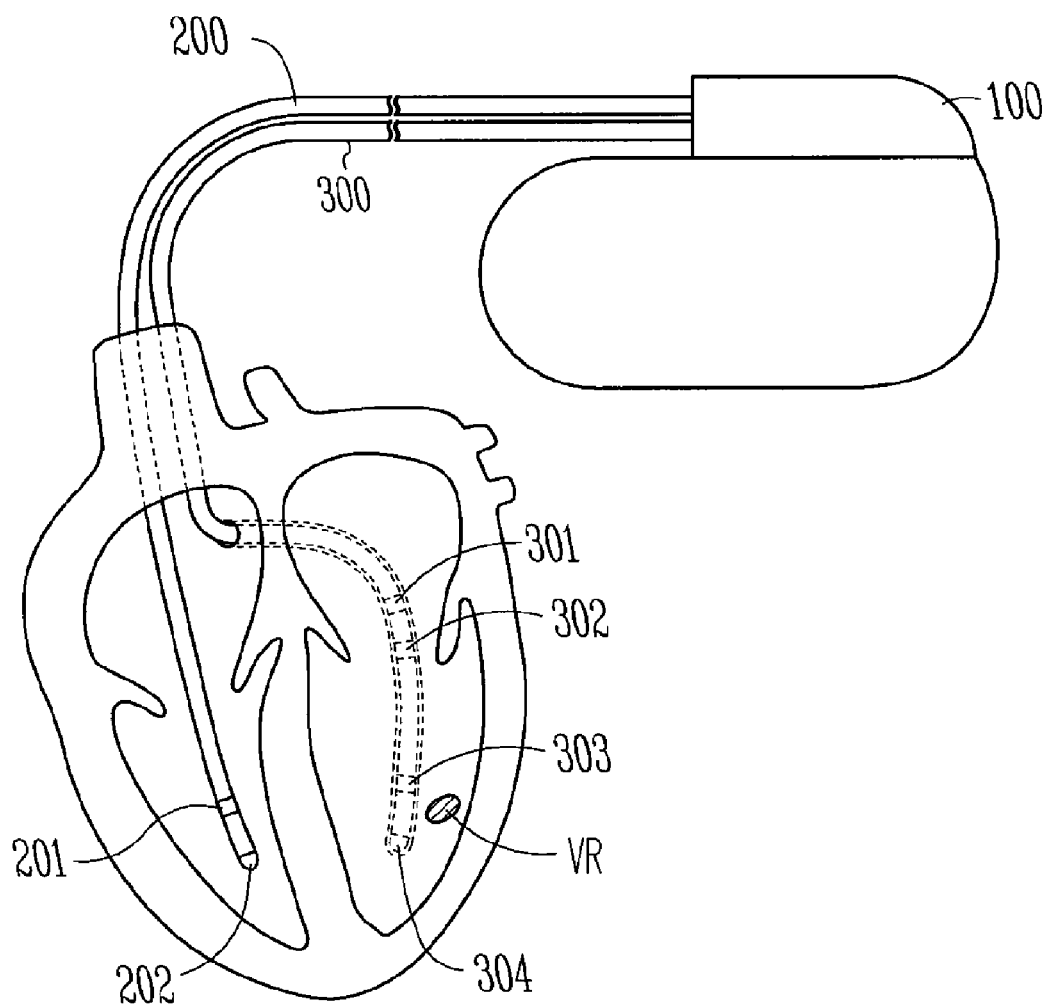
FIG. 1 illustrates the physical configuration of an exemplary pacing device.

Described herein is a method and device for delivering electrical stimulation to the heart in a manner that advantageously redistributes myocardial stress during systole for therapeutic purposes in the treatment of, for example, patients with ischemic heart disease, post-MI patients, and HF patients. Myocardial regions that contract earlier during systole experience less wall stress than later contracting regions. Pacing pulses may be delivered to a particular myocardial region to pre-excite that region relative to other regions during systole, with the latter being excited by intrinsic activation or a subsequent pacing pulse. As compared with an intrinsic contraction, the pre-excited region is mechanically unloaded or de-stressed, while the later excited regions are subjected to increased stress. Such pre-excitation pacing may be applied to deliberately de-stress a particular myocardial region that may be expected to undergo deleterious remodeling, such the area around a myocardial infarct or a hypertrophying region. Pre-excitation pacing may also be applied to deliberately stress a region remote from the pre-excitation pacing site in order to exert a conditioning effect, similar to the beneficial effects of exercise. Whether for intentionally stressing or de-stressing a myocardial region, such cardioprotective pre-excitation pacing may be applied intermittently, either according to a defined schedule or upon detection of specified entry or exit conditions.

As explained above, pacing pulses may be used to pre-excite a region of the heart so that it contracts before later-excited regions and experiences less stress during systole. This is in contradistinction to the normal physiological situation where, due the heart's specialized conduction system, the spread of depolarization throughout the myocardium is very rapid and results in a so-called synchronous contraction. If the contractility of the myocardial tissue is normal, a synchronous contraction is hemodynamically more effective in pumping blood. Cardiac resynchronization pacing attempts to restore synchronous contractions in patients having ventricular conduction abnormalities by delivering pacing pulses to the heart in a manner that results in a more synchronous contraction than would otherwise occur. Pre-excitation pacing applied to stress or de-stress a particular myocardial region for a cardioprotective effect, on the other hand, is the delivery of pacing pulses in a manner that causes a dyssynchronous contraction. Such dyssynchronous contractions are responsible for the desired cardioprotective effects of pre-excitation pacing but may also be hazardous. Described herein is a method and system that uses measures of ventricular dyssynchrony or a patient's physiological response to ventricular dyssynchrony to control the delivery of cardioprotective pre-excitation pacing in closed-loop fashion.

Mechanical Effects of Pacing Therapy

When the ventricles are stimulated to contract by a pacing pulse applied through an electrode located at a particular pacing site, the excitation spreads from the pacing site by conduction through the myocardium. This is different from the normal physiological situation, where the spread of excitation to the ventricles from the AV node makes use of the heart's specialized conduction system made up of Purkinje fibers which allows a rapid and synchronous excitation of the entire ventricular myocardium. The excitation resulting from a pacing pulse, on the other hand, produces a relatively asynchronous contraction due to the slower velocity at which excitation is conducted from the pacing site to the rest of the myocardium. Regions of the myocardium located more distally from the pacing site are thus excited later than regions proximal to the pacing site as compared with an intrinsic contraction. As explained below, this results in a re-distribution of myocardial wall stress.

The degree of tension on a muscle fiber before it contracts is termed the preload, while the degree of tension on a muscle fiber as it contracts is termed the afterload. Increasing the preload stretches a muscle fiber and also increases its maximum tension and velocity of shortening during contraction. With respect to the heart, the preload of a particular myocardial region is the myocardial wall stress at the end of diastole due to end-diastolic pressure and the forces applied by adjacent regions. The afterload of a myocardial region is the myocardial wall stress during systole due to the pressure load that the heart must pump against. When a myocardial region contracts late relative to other regions, the contraction of those other regions stretches the later contracting region and increases its preloading, thus causing an increase in the contractile force generated by the region. Conversely, a myocardial region that contracts earlier relative to other regions experiences decreased preloading and generates less contractile force. Because pressure within the ventricles rises rapidly from a diastolic to a systolic value as blood is pumped out into the aorta and pulmonary arteries, the parts of the ventricles that contract earlier during systole do so against a lower afterload than do parts of the ventricles contracting later. Delivery of a pacing pulse to a ventricular region makes that region contract earlier than other parts of the ventricle. The paced region will therefore be subjected to both a decreased preload and afterload which decreases the mechanical stress experienced by the region relative to other regions during systolic contraction. A region remote from the paced region, on the other hand, will experience increased mechanical stress as it contracts later during systole due to either conduction from the pre-excited site, a subsequent pace applied to the remote region, or intrinsic activation conducted from the AV node.

Applications of Stress Reducing Pre-excitation Pacing

All but a small fraction of the total amount of oxygen consumed by the myocardium is for the purpose of active muscular contraction during systole, and the oxygen demand of a particular myocardial region increases with increasing systolic wall stress. Causing a particular myocardial region to contract earlier relative to other regions will thus lessen its metabolic demands and the degree of any ischemia that may be present. Particular myocardial regions may also be vulnerable to undergoing deleterious remodeling as a result of increased wall stress in post-MI or HF patients. In order to cause early contraction and lessened stress to a myocardial region vulnerable to becoming ischemic or undergoing remodeling, pre-excitation pacing pulses may be delivered to one or more sites in or around the vulnerable region in a manner that pre-excites those sites relative to the rest of the ventricle and mechanically unloads the vulnerable region. Pre-excitation pacing therapy to unload a vulnerable region may be implemented by pacing the ventricles at a single site in proximity to the vulnerable region or by pacing at multiple ventricular sites in such proximity. In the latter case, the pacing pulses may be delivered to the multiple sites simultaneously or in a defined pulse output sequence. The single-site or multiple site pacing may be performed in accordance with a bradycardia pacing algorithm such as an inhibited demand mode or a triggered mode.

Applications of Stress Augmenting Pre-excitation Pacing

Another use of pre-excitation pacing is to intentionally stress a region vulnerable to ischemia by pacing at a site(s) remote from the vulnerable region. As described above, such pacing causes increased mechanical stress to the vulnerable region by delaying its contraction during systole relative to other regions. Intermittently stressing a vulnerable region may cause a low level of myocardial ischemia in the region in a patient with demand ischemia, thereby promoting angiogenesis and pre-conditioning the vulnerable region to better withstand the effects of a subsequent ischemic episode. Stress augmentation pacing may also be applied to a weakened region or to a large part of the myocardium in the form of an asynchronous contraction in order to exert a pre-conditioning effect similar to exercise. Pre-excitation pacing therapy to augment stress may be implemented by pacing the ventricles at a single site or multiple sites remote from the region(s) desired to be stressed in accordance with a bradycardia pacing algorithm such as an inhibited demand mode or a triggered mode. Multiple pacing pulses may be delivered to the multiple sites simultaneously or in a defined pulse output sequence.

Exemplary Implantable Device

FIG. 1 shows an exemplary implantable cardiac device 100 for delivering pre-excitation pacing for the purpose of stressing or de-stressing one or more myocardial regions. In addition, the device may have the capability of delivering other types of pacing therapy such as bradycardia pacing and cardiac resynchronization pacing. As will be described below, the device may be configured to switch between a normal operating mode and a pre-excitation mode for delivering pre-excitation pacing in accordance with defined entry and exit conditions. Implantable pacing devices are typically placed subcutaneously or submuscularly in a patient's chest with leads threaded intravenously into the heart to connect the device to electrodes disposed within a heart chamber that are used for sensing and/or pacing of the chamber. Electrodes may also be positioned on the epicardium by various means. A programmable electronic controller causes the pacing pulses to be output in response to lapsed time intervals and/or sensed electrical activity (i.e., intrinsic heart beats not as a result of a pacing pulse). The device senses intrinsic cardiac electrical activity through one or more sensing channels, each of which incorporates one or more of the electrodes. In order to excite myocardial tissue in the absence of an intrinsic beat, pacing pulses with energy above a certain threshold are delivered to one or more pacing sites through one or more pacing channels, each of which incorporates one or more of the electrodes. FIG. 1 shows the exemplary device having two leads 200 and 300, each of which is a multi-polar (i.e., multi-electrode) lead having electrodes 201-202 and 301-304, respectively. The electrodes 201-202 are disposed in the right ventricle in order to excite or sense right ventricular and/or septal regions, while the electrodes 301-304 are disposed in the coronary sinus or left cardiac veins in order to excite or sense regions of the left ventricle. If a region VR that is vulnerable to remodeling or ischemia were located in the apical region of the left ventricle, pre-excitation pacing to the region could be delivered via electrodes 303 and 304 in a bipolar pacing configuration to de-stress and unload the vulnerable region. Such pre-excitation pacing could be delivered, for example, as left ventricular-only pacing or as biventricular pacing with an offset such that the left ventricle is paced before the right. Conversely, if it were desired to deliberately stress the region VR for cardioprotective pre-conditioning, pre-excitation pacing could be delivered via electrodes 201 and 202 in a right ventricle-only pacing mode or electrodes 301 and 302 in a left ventricle-only or biventricular pacing mode in order to pre-excite a myocardial region remote from the region VR. Other embodiments may use any number of electrodes in the form of unipolar and/or multi-polar leads in order to excite different myocardial sites. As explained below, once the device and leads are implanted, the pacing and/or sensing channels of the device may be configured with selected ones of the multiple electrodes in order to selectively pace or sense a particular myocardial site(s).

Figure 2:
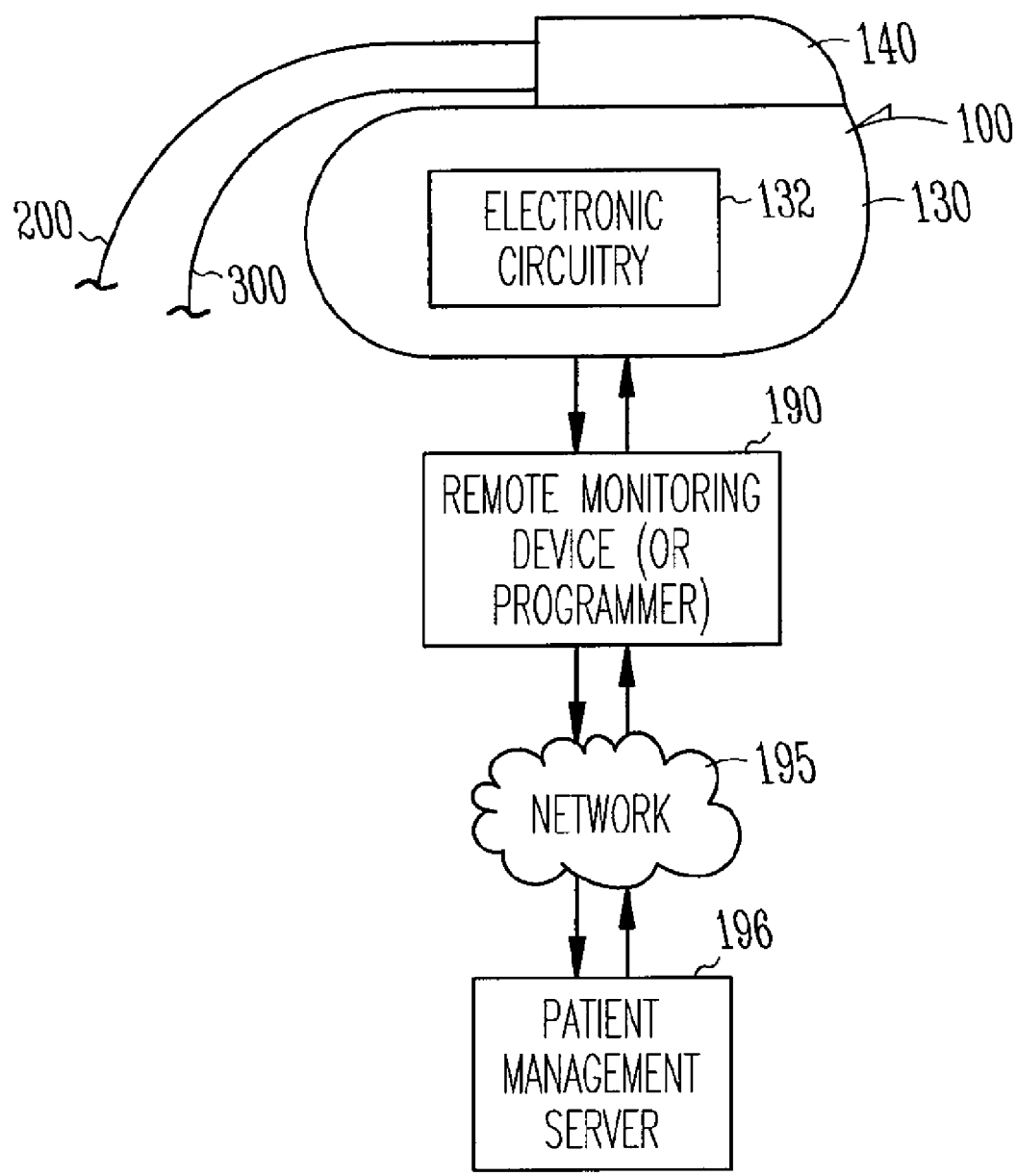
FIG. 2 shows the components of an exemplary device.

FIG. 2 shows the components of the implantable device 100 in more detail as well as an exemplary monitoring/programming system. The implantable device 100 includes a hermetically sealed housing 130 that is placed subcutaneously or submuscularly in a patient's chest. The housing 130 may be formed from a conductive metal, such as titanium, and may serve as an electrode for delivering electrical stimulation or sensing in a unipolar configuration. A header 140, which may be formed of an insulating material, is mounted on the housing 130 for receiving leads 200 and 300 which may be then electrically connected to pulse generation circuitry and/or sensing circuitry. Contained within the housing 130 is the electronic circuitry 132 for providing the functionality to the device as described herein which may include a power supply, sensing circuitry, pulse generation circuitry, a programmable electronic controller for controlling the operation of the device, and a telemetry transceiver capable of communicating with an external programmer or a remote monitoring device 190. An external programmer wirelessly communicates with the device 100 and enables a clinician to receive data and modify the programming of the controller. A remote monitoring device also communicates via telemetry with the device 100 and may be further interfaced to a network 195 (e.g., an internet connection) for communicating with a patient management server 196 that allows clinical personnel at remote locations to receive data from the remote monitoring device as well as issue commands. The controller may be programmed such when particular conditions are detected by the monitoring circuitry (such as when a measured parameter exceeds or falls below a specified limit value), the device transmits an alarm message to the remote monitoring device and to the patient management server to alert clinical personnel.

Figure 3:
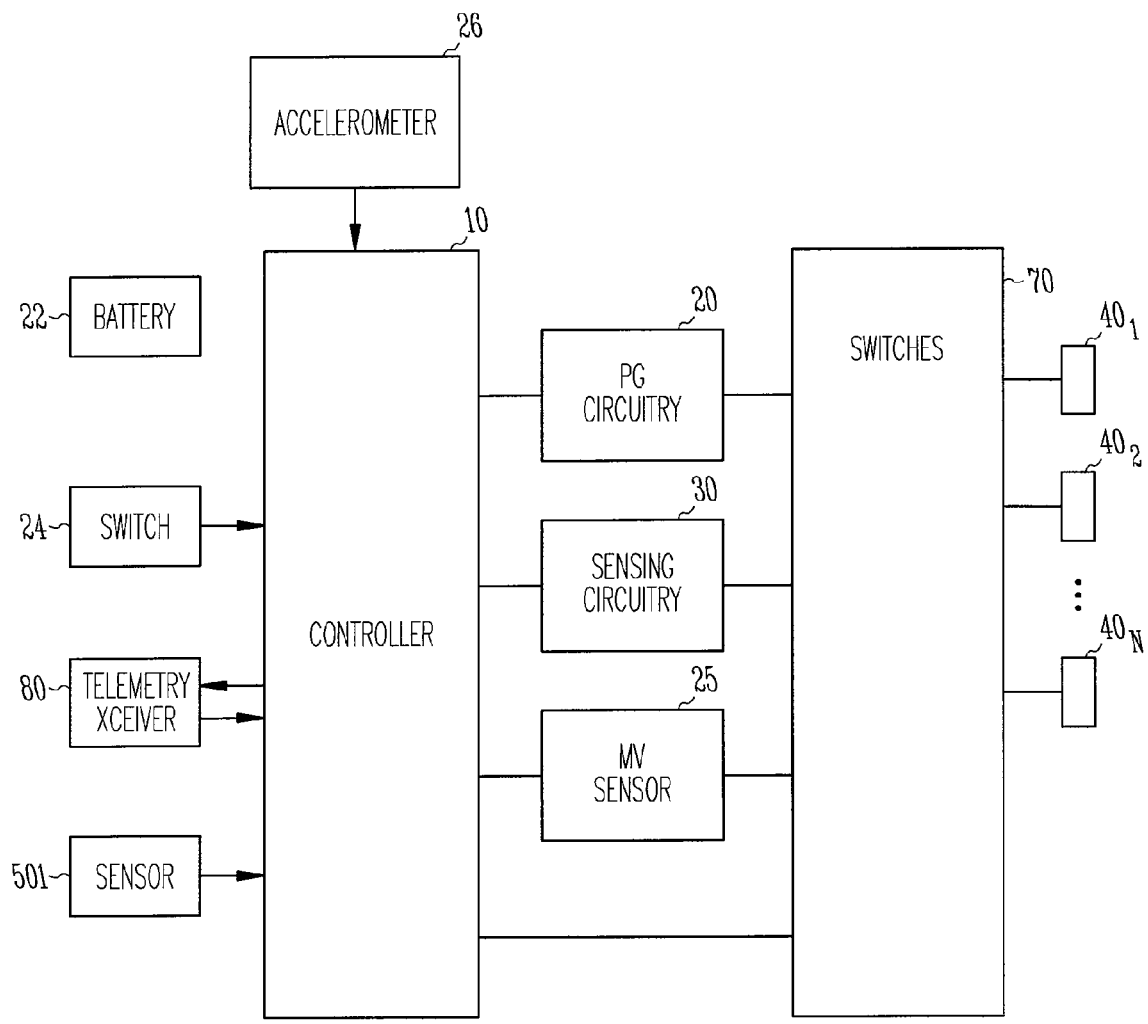
FIG. 3 is a block diagram of the electronic circuitry of an exemplary device.

A block diagram of the circuitry 132 is illustrated in FIG. 3. A battery 22 supplies power to the circuitry. The controller 10 controls the overall operation of the device in accordance with programmed instructions and/or circuit configurations. The controller may be implemented as a microprocessor-based controller and include a microprocessor and memory for data and program storage, implemented with dedicated hardware components such as ASICs (e.g., finite state machines), or implemented as a combination thereof. The controller also includes timing circuitry such as external clocks for implementing timers used to measure lapsed intervals and schedule events. As the term is used herein, the programming of the controller refers to either code executed by a microprocessor or to specific configurations of hardware components for performing particular functions. A telemetry transceiver 80 is interfaced to the controller which enables the controller to communicate with an external programmer and/or a remote monitoring unit. A magnetically or tactilely actuated switch 24 is also shown as interfaced to the controller to allow the patient to signal certain conditions or events to the implantable device. Sensing circuitry 30 and pulse generation circuitry 20 are interfaced to the controller by which the controller interprets sensing signals and controls the delivery of pacing pulses in accordance with a pacing mode. The sensing circuitry 30 receives atrial and/or ventricular electrogram signals from sensing electrodes and includes sensing amplifiers, analog-to-digital converters for digitizing sensing signal inputs from the sensing amplifiers, and registers that can be written to for adjusting the gain and threshold values of the sensing amplifiers. The pulse generation circuitry 20 delivers pacing pulses to pacing electrodes disposed in the heart and includes capacitive discharge pulse generators, registers for controlling the pulse generators, and registers for adjusting pacing parameters such as pulse energy (e.g., pulse amplitude and width). The device allows adjustment of the pacing pulse energy in order to ensure capture of myocardial tissue (i.e., initiating of a propagating action potential) by a pacing pulse. The pulse generation circuitry may also include a shocking pulse generator for delivering a defibrillation/cardioversion shock via a shock electrode upon detection of a tachyarrhythmia.

Myocardial sites in proximity to an ischemic region may be less excitable than normal and require an increased pacing energy in order to achieve capture. Pacing pulse energies for pre-exciting ischemic regions may be adjusted by programming the device via the telemetry interface in accordance with electrophysiological testing to determine an appropriate pacing pulse energy. The implantable device may also incorporate autocapture, autothreshold, and reconfiguration functionality described in U.S. patent application Ser. No. 11/427,517, filed Jun. 29, 2006, which are especially useful for the delivery of pre-excitation pacing to a vulnerable region because the excitability characteristics of a vulnerable region may change over time.

A pacing channel is made up of a pulse generator connected to an electrode, while a sensing channel is made up of a sense amplifier connected to an electrode. Shown in the figure are electrodes $40_1$ through $40_N$ where N is some integer. The electrodes may be on the same or different leads and are electrically connected to a MOS switch matrix 70. The switch matrix 70 is controlled by the controller and is used to switch selected electrodes to the input of a sense amplifier or to the output of a pulse generator in order to configure a sensing or pacing channel, respectively. The device may be equipped with any number of pulse generators, amplifiers, and electrodes that may be combined arbitrarily to form sensing or pacing channels. The switch matrix 70 allows selected ones of the available implanted electrodes to be incorporated into sensing and/or pacing channels in either unipolar or bipolar configurations. A bipolar sensing or pacing configuration refers to the sensing of a potential or output of a pacing pulse between two closely spaced electrodes, where the two electrodes are usually on the same lead (e.g., a ring and tip electrode of a bipolar lead or two selected electrodes of a multi-polar lead). A unipolar sensing or pacing configuration is where the potential sensed or the pacing pulse output by an electrode is referenced to the conductive device housing or another distant electrode.

The device illustrated in FIG. 3 may be configured with multiple sensing and/or pacing channels that may be either atrial or ventricular channels depending upon the location of the electrode. The device is therefore capable of delivering single-site or multiple site ventricular pre-excitation pacing for purposes of stress reduction/augmentation as well as conventional pacing. The switch matrix allows particular myocardial sites to be pre-excited for purposes of stress reduction or augmentation by selecting the appropriately disposed electrode(s) to be incorporated into a pacing channel used to deliver pre-excitation pacing. Configuration of pacing and sensing channels may be performed via an external programmer communicating through the telemetry interface as well as automatically by the device when switching to or from different pacing modes.

Pre-excitation pacing may be delivered as single-site pacing, biventricular pacing where one of the ventricles is pre-excited relative to the other as determined by a programmed biventricular offset interval, or delivered as multi-site ventricular pacing. In the case where the pre-excitation pacing is delivered at multiple sites, the sites may be paced simultaneously or in accordance with a particular pulse output sequence that specifies the order and timing in which the sites are to be paced during a single beat. When an electrogram signal in an atrial or ventricular sensing channel exceeds a specified threshold, the controller detects an atrial or ventricular sense, respectively, which pacing algorithms may employ to trigger or inhibit pacing. The controller is capable of operating the device in a number of programmed modes where a programmed mode defines how pacing pulses are output in response to sensed events and expiration of time intervals. Pre-excitation pacing of one or more ventricular sites in proximity to, or remote from, a vulnerable region may be delivered in conjunction with a bradycardia pacing mode, which refers to a pacing algorithm that enforces a certain minimum heart rate, and may include or not include pacing pulses delivered to the atria or ventricles for other purposes (e.g., treatment of bradycardia). Inhibited demand bradycardia pacing modes utilize escape intervals to control pacing in accordance with sensed intrinsic activity. In an inhibited demand ventricular pacing mode, the ventricle is paced during a cardiac cycle only after expiration of a defined escape interval during which no intrinsic beat by the chamber is detected. For example, a ventricular escape interval can be defined between ventricular events so as to be restarted with each ventricular sense or pace, referred to as a lower rate interval (LRI). The inverse of this escape interval is the minimum rate at which the pacemaker will allow the ventricles to beat, sometimes referred to as the lower rate limit (LRL). Paces may also be delivered in a rate-adaptive pacing mode where the escape intervals are modified in accordance with a measured exertion level such as with accelerometer 26 or minute ventilation sensor 25. In atrial tracking and AV sequential pacing modes, another ventricular escape interval is defined between atrial and ventricular events, referred to as the atrio-ventricular or AV interval. The atrio-ventricular interval is triggered by an atrial sense or pace and stopped by a ventricular sense or pace. A ventricular pace is delivered upon expiration of the atrio-ventricular interval if no ventricular sense occurs before the expiration.

In order for pre-excitation pacing to cause early contraction of a paced region relative to other regions located remotely from the pre-excitation site, the latter regions should not be excited until later during systole. In a patient without intact native AV conduction (i.e., an AV block), such later excitation may be accomplished by either spread of the depolarization resulting from pre-excitation to the remote site or application of a subsequent pace if necessary. On the other hand, if native AV conduction is intact and the pre-excitation mode delivers pre-excitation pacing in an atrial tracking or AV sequential pacing mode, the AV delay interval should be selected to be short enough relative to the patient's intrinsic AV interval that the pre-excited site depolarizes well before remotely located regions depolarize due to intrinsic AV conduction. Delivering pre-excitation pacing with a shortened AV interval relative to the patient's intrinsic AV interval (e.g., 30-80% of the intrinsic interval) facilitates pre-excitation by allowing the pre-excitation depolarization to spread beyond the pre-excited site and excite the rest of the myocardium without interference from intrinsic excitation conducted from the AV node. In these cases, the shorter the AV delay interval is relative to the patient's intrinsic AV interval, the more the paced site is pre-excited. In one embodiment, the device is configured to dynamically shorten the AV delay interval in the pre-excitation mode in accordance with a sensed variable that is correlated with the presence of myocardial ischemia such as described above in order to provide more stress reducing pre-excitation as it is needed. For example, the AV delay interval could be shortened in accordance with measured heart rate or exertion level. Shortening the AV delay interval in this manner also compensates for the physiological shortening of the patient's intrinsic AV interval that occurs with increasing heart rate.

Mode Switching

As described above, an implantable pacing device may have the capability of configuring multiple sensing and/or pacing channels using multiple electrodes that can be implanted at selected myocardial sites in the form of unipolar, bipolar, or multipolar leads. The device may then operate in a number of different operating modes, where an operating mode refers to the particular subset of the available electrodes that are configured into sensing and/or pacing channels and the pacing algorithm (i.e., pacing mode) used to determine the timing of the pacing pulses delivered by each pacing channel. If pacing electrodes are disposed at a pre-excitation pacing site(s) in proximity to a selected myocardial region and/or remote from the selected myocardial region, the device may be programmed to operate in a pre-excitation mode that delivers pre-excitation pacing pulses to the selected region in accordance with a programmed pacing mode for the purpose of de-stressing the selected region or for stressing a region(s) located remotely from the pre-excitation pacing site(s). The device may be programmed to operate in the pre-excitation mode continuously or intermittently. In the latter case, the device may revert to a normal mode when the pre-excitation mode terminates that may include any type of pacing (e.g., bradycardia or cardiac resynchronization pacing) or no pacing at all. Switching to the pre-excitation mode may involve configuring different pacing or sensing channels from those used during the normal mode as well as adjustment of particular pacing parameter such as shortening the AV delay interval used in AV sequential and atrial tracking pacing modes. The device may be configured to switch from the normal mode to the pre-excitation mode in accordance with one or more entry conditions and revert to the normal mode in accordance with one or more exit condition. Entry and exit conditions may also be used to switch between different pre-excitation modes that pre-excite different myocardial regions. For example, one pre-excitation mode may stress a particular region, while another pre-excitation mode may de-stress the same region. Examples of entry and exit conditions include: a lapsed time interval, actuation of a patient-operated switch that the patient may operate, receipt of a telemetry command, detection or non-detection of the presence of myocardial ischemia by the device in accordance with a sensed variable that is correlated with the presence of myocardial ischemia such as features derived from sensed cardiac electrical activity, or a sensed physiological variable being below or above a specified threshold value. The device may be equipped with appropriate sensors and configured to measure physiological variables such as heart rate, minute ventilation, activity level, blood pressure, cardiac output, cardiac impedance, and heart rate variability that can be used for entry and/or exit conditions. A composite entry and/or exit condition may also be formed by ANDing or ORing any of the conditions mentioned above in any desired manner.

Figure 4:
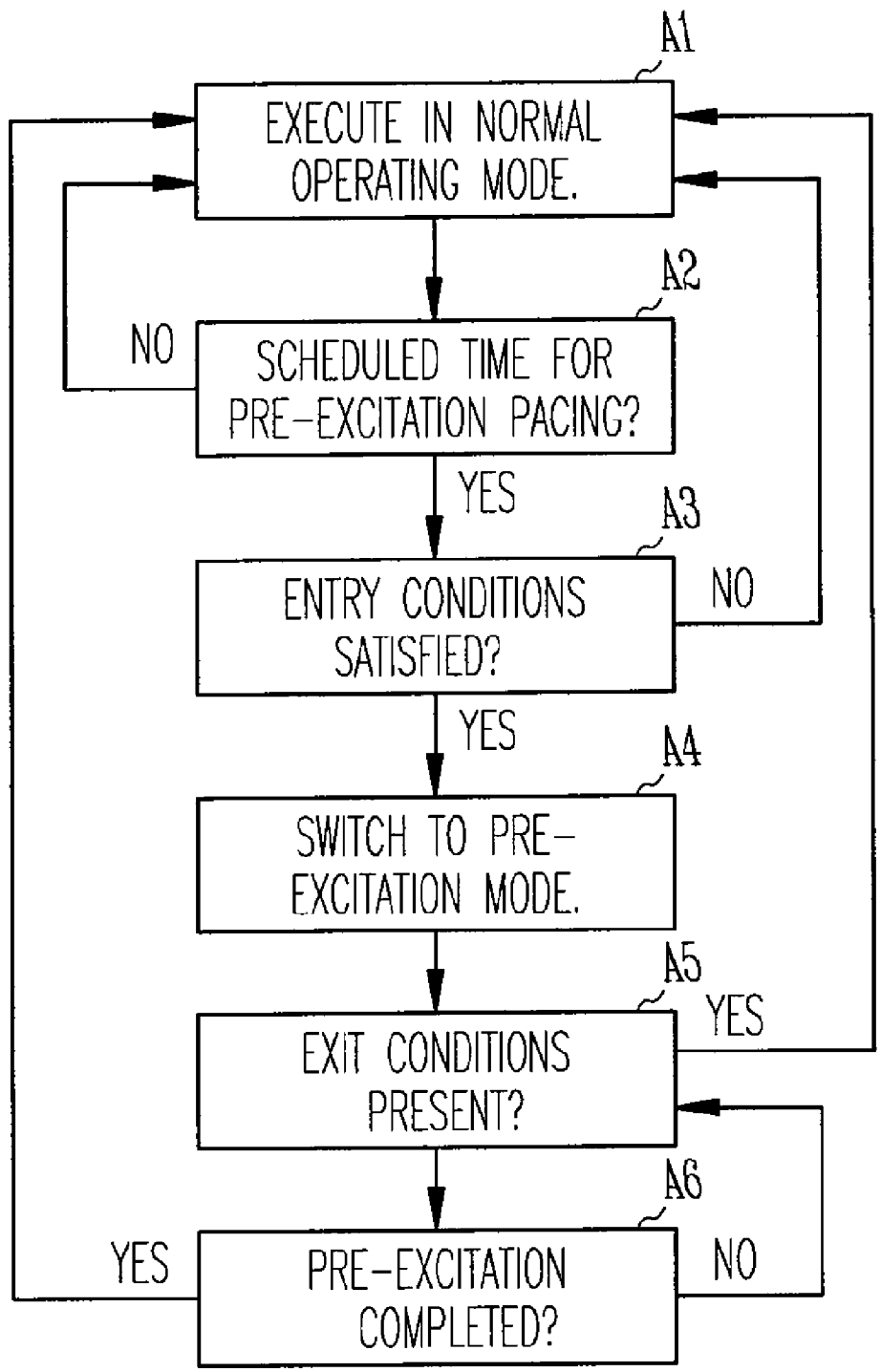
FIG. 4 illustrates an exemplary algorithm for switching between a normal mode and a pre-excitation mode.

FIG. 4 illustrates one way that pre-excitation pacing may be implemented by a cardiac device. In this embodiment, the controller of the device is programmed to transition through a number of different states, designated as A1 through A6. At state A1, the device operates in its normal operating mode. At state A2, while continuing to operate in state A1, the device determines whether it should switch to the pre-excitation mode based upon a lapsed time interval or a triggering condition. Optionally, the device may also be configured to test for one or more particular entry conditions before switching to the pre-excitation mode as implemented by state A3. Examples of entry conditions that must be satisfied before the switch to the pre-excitation mode include a measured exertion level being within a specified entry range, a measured heart rate being within a specified entry range, non-detection of cardiac arrhythmias, non-detection of cardiac ischemia, and actuation of a magnetically or tactilely actuated switch incorporated into the device by the patient that allows delivery of pre-excitation pacing. At state A3, the device checks to see if the one or more entry conditions are satisfied and returns to state A1 if not. If the appropriate entry conditions are satisfied, the device switches to the pre-excitation mode at state A4. The pre-excitation mode supercedes the normal operating mode to the extent necessary to carry out the pre-excitation pacing but may allow certain functions performed in the normal operating mode to continue. Alternatively, the pre-excitation mode could be said to incorporate particular functions of the normal operating mode, which functions are modified if necessary to deliver the pre-excitation pacing. While executing in the pre-excitation mode, the device may optionally be configured to monitor for one or more exit conditions which cause the device to revert to the normal operating mode. Such exit conditions could be the same or different from the entry conditions that must be satisfied before entering the pre-excitation mode. At state A5, while executing in the pre-excitation mode, the device monitors for the occurrence of one or more exit conditions such as a measured exertion level being outside a specified permissible range, a measured heart rate being outside a specified permissible range, presence of a cardiac arrhythmia, presence of cardiac ischemia, and actuation of a magnetically or tactilely actuated switch incorporated into the device by the patient to stop delivery of pre-excitation pacing. If an exit condition occurs, the device returns to the normal operating mode at state A1. Otherwise, the device proceeds to state A6 and checks to see if the prescribed amount and/or duration of pre-excitation pacing has been delivered. If the specified amount or duration of pre-excitation pacing has been delivered, the device returns to state A1 and resumes the normal operating mode. Otherwise, the device loops back to state A5 to monitor for exit conditions.

Closed-loop Control of Pre-excitation Pacing

Ventricular dyssynchrony is the desired result of pre-excitation pacing to redistribute myocardial stress for a cardioprotective effect. Such dyssynchrony is what is responsible for causing the difference in stress experienced by the pre-excited and later-excited regions. Cardioprotective pre-excitation pacing may be applied, for example, to increase the stress of a myocardial region for a protective effect similar to exercise or applied to decrease the stress of a myocardial region to protect against remodeling. If too little dyssynchrony is produced by the pre-excitation pacing, the desired therapeutic effect will not be achieved. On the other hand, since a dyssynchronous ventricular contraction caused by pre-excitation pacing is usually less hemodynamically effective than a contraction without such pacing, an excessive amount of dyssynchrony may impair the heart's pumping ability to an intolerable extent. Described herein is a closed-loop system for controlling cardioprotective pre-excitation pacing in which the pre-excitation pacing is adjusted in accordance with an index computed as a function of one or more physiological variables that are reflective of ventricular dyssynchrony. The physiological variables used to compute the index may be either directly reflective of the degree of ventricular dyssynchrony produced by the pre-excitation pacing or reflective of a patient's physiological response to the ventricular dyssynchrony. Examples of physiological variables that are reflective of ventricular dyssynchrony, which may be either numerical measures of a particular quantity or an indication of a particular condition, include variables relating to: a QRS width of an electrogram, a QT interval of an electrogram, a time interval between electrically sensed contractions of different myocardial sites, a time interval between mechanically sensed contractions of different myocardial sites, the presence or absence of one or more particular heart sounds, cardiac output, cardiac wall motion, blood oxygen level, blood pH, heart rate, heart rate variability, timing of myocardial impedance changes, activity level, minute ventilation, and blood pressure. The device illustrated in FIG. 3 may be configured to use its sensing channels and available sensing modalities for sensing such physiological variables and/or be equipped with appropriate additional sensing modalities as represented by a dyssynchrony sensor 501 in FIG. 3. Such sensing modalities may also be incorporated into an external monitor configured to communicate with the implantable device via telemetry. The function used to compute the index from the physiological variables may be a linear mapping (e.g., a weighted average) or a non-linear mapping, either of which may be implemented as a formula or as a look-up table that maps particular combinations of physiological variable values to particular index values. The function may also be vector-valued so that the index is a vector having separate values for a plurality of different axes. As described below, such an index may be computed in a manner that either emphasizes the amount of cardioprotection being provided by the cardioprotective pre-excitation pacing or emphasizes the physiological stress that the patient is being subjected to, referred to as a protective index and a stress index, respectively. In order to control the amount of cardioprotective pacing delivered by the device in accordance with the computed index, the device controller may be programmed to modify one or more parameters that affect the amount of ventricular dyssynchrony produced by the cardioprotective pacing, referred to herein as cardioprotection parameters. Examples of such cardioprotection parameters include: the duty cycle of the cardioprotective mode (e.g., as defined by entry and exit conditions based on lapsed time intervals), a pacing site or sites used in the cardioprotective mode, a pacing algorithm used in the cardioprotective mode, a pacing rate used in the cardioprotective mode, pacing amplitude, pacing pulse duration, pacing vector, pacing sequence of multiple pacing sites, VV delay(s) between multiple ventricular paces, and the value of an AV delay used in the cardioprotective mode.

In one embodiment, the physiological parameters reflective of ventricular dyssynchrony are mapped to an index designed to provide a measure of the effectiveness of the ventricular dyssynchrony in producing the desired cardioprotective effect, referred to as a protective index. The particular cardioprotective effect that results from ventricular dyssynchrony depends on how the cardioprotective pre-excitation pacing is applied and upon the individual patient. For example, the cardioprotective pre-excitation pacing could be applied to de-stress a region vulnerable to ischemia to protect against ischemia or possible infarction, to stress a region vulnerable to ischemia for a conditioning effect, to stress a region weakened by infarct for a conditioning effect, to de-stress a region weakened by infarct to prevent remodeling, to de-stress a hypertrophied region to prevent remodeling, and/or to elicit physiological responses to the ventricular dyssynchrony that mimic exercise. A protective index mapping function may be constructed for an individual patient that weights the physiological parameters in a manner so that the protective index most accurately reflects the amount of cardioprotection being received. Such a mapping function may be constructed, for example, in accordance with empirical data collected during clinical testing of the patient while cardioprotective pre-excitation pacing is being delivered. The protective index thus derived may then be used in a closed-loop system that controls the amount of ventricular dyssynchrony produced by the cardioprotective pre-excitation pacing.

In order to control the amount of ventricular dyssynchrony produced by cardioprotective pre-excitation pacing, one or more of the cardioprotection parameters listed above may be adjusted on a continuous or periodic basis in a manner that tends to maintain the protective index at some specified value, referred to as a desired protection level value. (If the protective index is a vector, the desired protection level value is also a vector.) Such a control scheme thus ensures that the patient receives the desired amount of cardioprotection from the pre-excitation pacing as measured by the protective index. The cardioprotection parameters may be adjusted according to a mapping function that maps particular protective index values (or deviations of the protective index from the desired protection level value) to particular sets of cardioprotection parameter values. Alternatively, one or more parameter-specific protective indexes could be computed for adjusting particular cardioprotection parameters or groups of such parameters. In that case, a corresponding desired protection level value could be specified for each parameter-specific protective index. Different parameter-specific indexes could also be computed using physiological parameters collected over different time frames. For example, the AV delay could be adjusted in accordance with a parameter-specific protective index computed from instantaneously collected physiological parameter values, while the duty-cycle of the cardioprotective mode could be adjusted in accordance with a parameter-specific index computed from physiological parameter values averaged over some specified period of time.

In another embodiment, another index may be computed from one or more physiological parameter values reflective of ventricular dyssynchrony that is designed to reflect the patient's condition from a safety point of view, referred to as a stress index. A stress index mapping function may be constructed for an individual patient that weights the physiological parameters in a manner so that the stress index most accurately reflects the amount of potentially unsafe physiological stress that the patient is being subjected to by the cardioprotective pre-excitation pacing. Similar to the protective index described above, a mapping function for the stress index may be constructed in accordance with empirical data collected during clinical testing of the patient while cardioprotective pre-excitation pacing is being delivered. Although the stress index and the protective index may be computed from the same or different physiological parameter values, the two indexes will in most cases use different weightings for the physiological parameter values to reflect the different purposes of the indexes. While the protective index is designed to measure the amount of cardioprotection being provided to the patient, the stress index is designed to provide a measure of the stress to which the patient is being subjected that could be dangerous if in a specified range, referred to as the stress limit range. For example, the stress limit range could be defined as the values of the stress index being above a specified stress limit value. If the stress index is found to be in the stress limit range, indicating that the patient may be being subjected to a dangerous level of physiological stress, the desired protection level value may be adjusted to decrease the amount of ventricular dyssynchrony produced by the pre-excitation pacing.

Figure 5:
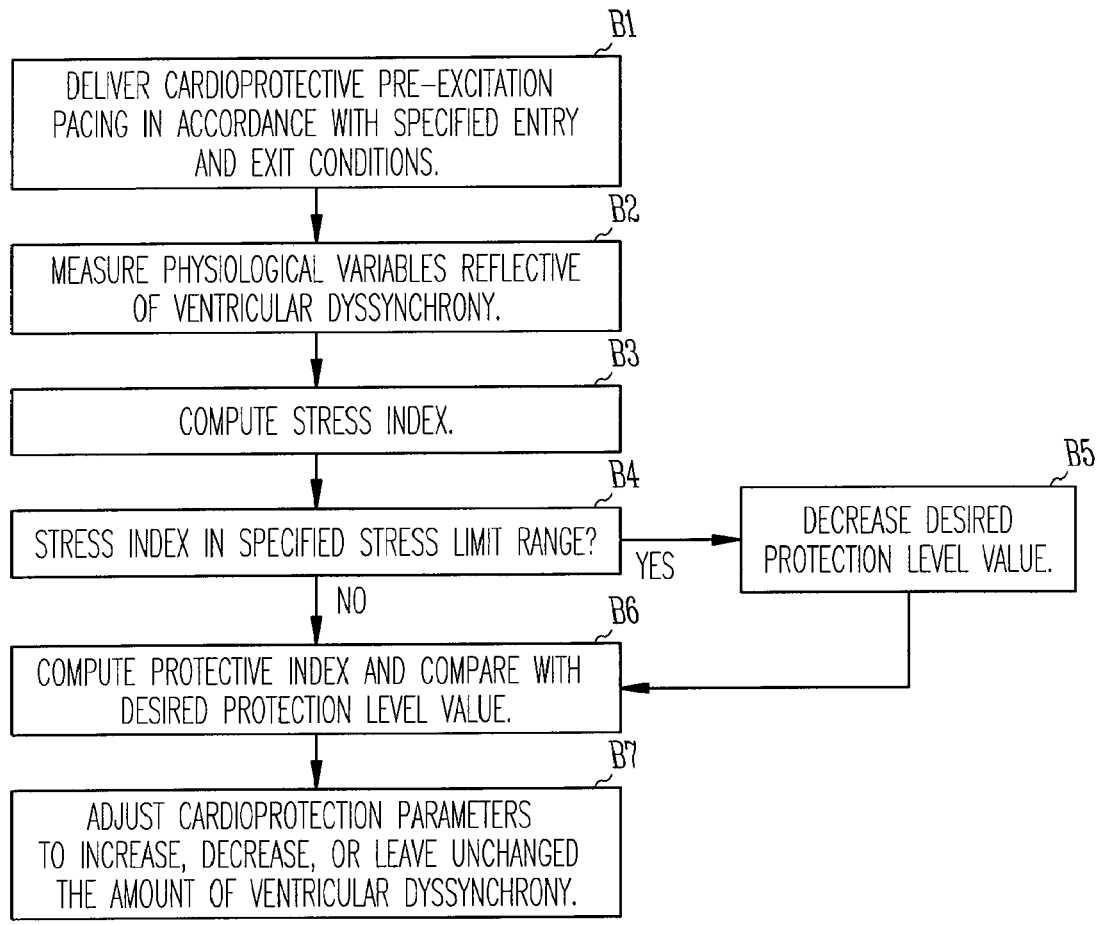
FIG. 5 illustrates an exemplary scheme for controlling cardioprotective pre-excitation pacing in closed-loop fashion.

FIG. 5 illustrates an exemplary control scheme for controlling cardioprotective pre-excitation pacing that utilizes a protective index and a stress index. At step B1, the implantable cardiac device delivers cardioprotective pre-excitation pacing in accordance with specified entry and exit conditions, and physiological variables reflective of ventricular dyssynchrony are measured at step B2. A stress index is computed at step B3 and compared with a specified stress limit range at step B4. If the stress index is in the stress limit range, the desired protection level value is decreased at step B5. (It is assumed in this embodiment that a decreased desired protection level value corresponds to decreased ventricular dyssynchrony.) At step B6, a protective index is computed from the measured physiological variables reflective of ventricular dyssynchrony and compared with the desired protection level value. At step B7, one or more cardioprotection parameters are adjusted to increase, decrease, or leave unchanged the amount of ventricular dyssynchrony produced by the pre-excitation pacing so as to maintain the protective index at the desired protection level value.

Any of the schemes for controlling cardioprotective pre-excitation pacing as described above may be implemented in the programming of the implantable cardiac device controller and/or in the programming of an external programmer that communicates with the implantable cardiac device via telemetry. For example, in one embodiment, the implantable device controller is programmed to continuously or periodically adjust one or more cardioprotection parameters in accordance with one or more protective indexes computed from physiological variables reflective of ventricular dyssynchrony in a manner that tends to maintain each protective index at a specified protection level value. A stress index may also be computed and used to adjust the desired protection level value as described above. In another embodiment, an external programmer collects physiological parameter values reflective of ventricular dyssynchrony from the implantable device via telemetry and/or by other means. The external programmer then computes the protective index (and possibly a stress index) and programs the implantable device via telemetry to adjust one or more cardioprotection parameters in a manner that tends to maintain the protective index at the desired protection level value.

The invention has been described in conjunction with the foregoing specific embodiments. It should be appreciated that those embodiments may also be combined in any manner considered to be advantageous. Also, many alternatives, variations, and modifications will be apparent to those of ordinary skill in the art. Other such alternatives, variations, and modifications are intended to fall within the scope of the following appended claims.

What is claimed is:

1. A cardiac device, comprising:
   one or more pacing channels for delivering pacing pulses to one or more myocardial sites;
   a controller programmed to operate the device in either a normal operating mode or to deliver cardioprotective pacing in a cardioprotective mode;
   wherein, in the cardioprotective mode, the controller is programmed to deliver paces to the one or more myocardial sites using a pacing mode that results in some degree of ventricular dyssynchrony as compared with the normal operating mode;
   wherein the controller is programmed to periodically or intermittently switch from the normal operating mode to the cardioprotective mode according to exit and entry conditions;
   a plurality of sensors for sensing physiological variables reflective of either the degree of ventricular dyssynchrony or a patient's physiological response to the ventricular dyssynchrony produced by the cardioprotective pacing;
   wherein the controller is programmed to compute a stress index as a function of one or more of the sensed physiological variables;
   wherein the controller is programmed to compute a protective index as a function of one or more of the sensed physiological variables;
   wherein the controller is programmed to modify one or more cardioprotection parameters that affect the amount of ventricular dyssynchrony produced by the cardioprotective pacing in a manner that tends to maintain the protective index at a specified desired protection level value; and,
   wherein the controller is programmed to compare the computed stress index with a specified stress limit range and to adjust the desired protection level value to decrease the amount of ventricular dyssynchrony produced by the cardioprotective pacing if the stress index is in the specified stress limit range.

2. The device of claim 1 wherein the one or more cardioprotection parameters affecting the amount of ventricular dyssynchrony produced by the cardioprotective pacing are selected from a group that includes the duty cycle of the cardioprotective mode, a pacing site or sites used in the cardioprotective mode, a pacing algorithm used in the cardioprotective mode, a pacing rate used in the cardioprotective mode, pacing amplitude, pacing pulse duration, pacing vector, pacing sequence of multiple pacing sites, VV delay(s) between multiple ventricular paces, and the value of an AV delay used in the cardioprotective mode.

3. The device of claim 1 wherein the protective index is computed as a function of one or more physiological variables selected from a group that includes a QRS width of an electrogram, QT interval of an electrogram, a time interval between electrically sensed contractions of different myocardial sites, a time interval between mechanically sensed contractions of different myocardial sites, the presence or absence of one or more particular heart sounds, cardiac output, cardiac wall motion, blood oxygen level, blood pH, heart rate variability, timing of myocardial impedance changes, and blood pressure.

4. The device of claim 1 wherein the stress index is computed as a function of one or more physiological variables selected from a group that includes a QRS width of an electrogram, QT interval of an electrogram, a time interval between electrically sensed contractions of different myocardial sites, a time interval between mechanically sensed contractions of different myocardial sites, the presence or absence of one or more particular heart sounds, cardiac output, cardiac wall motion, blood oxygen level, blood pH, heart rate variability, timing of myocardial impedance changes, and blood pressure.

5. The device of claim 1 wherein the controller is programmed to compute a separate parameter-specific protective index for adjusting each of a plurality of cardioprotection parameters in accordance therewith.

6. The device of claim 1 wherein the controller is programmed to map the deviation of the protective index from the desired protection level value to a plurality of cardioprotection parameters.

7. The device of claim 1 wherein the protective index and desired protection level values are vectors.

8. A method, comprising:
delivering pacing pulses to one or more myocardial sites in either a normal operating mode or in a cardioprotective mode;
wherein, in the cardioprotective mode, paces are delivered to the one or more myocardial sites using a pacing mode that results in some degree of ventricular dyssynchrony as compared with the normal operating mode;
periodically or intermittently switching from the normal operating mode to the cardioprotective mode according to exit and entry conditions;
sensing physiological variables reflective of either the degree of ventricular dyssynchrony or a patient's physiological response to the ventricular dyssynchrony produced by the cardioprotective pacing;
computing a stress index as a function of one or more of the sensed physiological variables;
computing a protective index as a function of one or more of the sensed physiological variables;
modifying one or more cardioprotection parameters that affect the amount of ventricular dyssynchrony produced by the cardioprotective pacing in a manner that tends to maintain the protective index at a specified desired protection level value; and,
comparing the computed stress index with a specified stress limit range and adjusting the desired protection level value to decrease the amount of ventricular dyssynchrony produced by the cardioprotective pacing if the stress index is in the specified stress limit range.

9. The method of claim 8 wherein the one or more cardioprotection parameters affecting the amount of ventricular dyssynchrony produced by the cardioprotective pacing are selected from a group that includes the duty cycle of the cardioprotective mode, a pacing site or sites used in the cardioprotective mode, a pacing algorithm used in the cardioprotective mode, a pacing rate used in the cardioprotective mode, pacing amplitude, pacing pulse duration, pacing vector, pacing sequence of multiple pacing sites, VV delay(s) between multiple ventricular paces, and the value of an AV delay used in the cardioprotective mode.

10. The method of claim 8 wherein the protective index is computed as a function of one or more physiological variables selected from a group that includes a QRS width of an electrogram, QT interval of an electrogram, a time interval between electrically sensed contractions of different myocardial sites, a time interval between mechanically sensed contractions of different myocardial sites, the presence or absence of one or more particular heart sounds, cardiac output, cardiac wall motion, blood oxygen level, blood pH, heart rate variability, timing of myocardial impedance changes, and blood pressure.

11. The method of claim 8 wherein the stress index is computed as a function of one or more physiological variables selected from a group that includes a QRS width of an electrogram, QT interval of an electrogram, a time interval between electrically sensed contractions of different myocardial sites, a time interval between mechanically sensed contractions of different myocardial sites, the presence or absence of one or more particular heart sounds, cardiac output, cardiac wall motion, blood oxygen level, blood pH, heart rate variability, timing of myocardial impedance changes, and blood pressure.

12. The method of claim 8 further comprising computing a separate parameter-specific protective index for adjusting each of a plurality of cardioprotection parameters in accordance therewith.

13. The method of claim 8 further comprising mapping the deviation of the protective index from the desired protection level value to a plurality of cardioprotection parameters.

14. The method of claim 8 wherein the protective index and the desired protection level value are vectors.

15. A system, comprising:
an implantable cardiac device having one or more pacing channels for delivering pacing pulses to one or more myocardial sites and a controller programmed to operate the device in either a normal operating mode or to deliver cardioprotective pacing in a cardioprotective mode;
wherein, in the cardioprotective mode, the controller is programmed to deliver paces to the one or more myocardial sites using a pacing mode that results in some degree of ventricular dyssynchrony as compared with the normal operating mode;
wherein the controller is programmed to periodically or intermittently switch from the normal operating mode to the cardioprotective mode according to exit and entry conditions;
a plurality of sensors for sensing physiological variables reflective of either the degree of ventricular dyssynchrony or a patient's physiological response to the ventricular dyssynchrony produced by the cardioprotective pacing;
an external programmer in communication with the implantable device via telemetry;
wherein the external programmer is programmed to compute a stress index as a function of one or more of the sensed physiological variables;
wherein the external programmer is programmed to compute a protective index as a function of one or more of the sensed physiological variables;
wherein the external programmer is programmed to modify one or more cardioprotection parameters that affect the amount of ventricular dyssynchrony produced by the cardioprotective pacing in a manner that tends to maintain the protective index at a specified desired protection level value; and, wherein the external programmer is programmed to compare the computed stress index with a specified stress limit range and to adjust the desired protection level value to decrease the amount of ventricular dyssynchrony produced by the cardioprotective pacing if the stress index is in the specified stress limit range.

16. The system of claim 15 wherein the one or more cardioprotection parameters affecting the amount of ventricular dyssynchrony produced by the cardioprotective pacing are selected from a group that includes the duty cycle of the cardioprotective mode, a pacing site or sites used in the cardioprotective mode, a pacing algorithm used in the cardioprotective mode, a pacing rate used in the cardioprotective mode, pacing amplitude, pacing pulse duration, pacing vector, pacing sequence of multiple pacing sites, VV delay(s) between multiple ventricular paces, and the value of an AV delay used in the cardioprotective mode.

17. The system of claim 15 wherein the protective index is computed as a function of one or more physiological variables selected from a group that includes a QRS width of an electrogram, QT interval of an electrogram, a time interval between electrically sensed contractions of different myocardial sites, a time interval between mechanically sensed contractions of different myocardial sites, the presence or absence of one or more particular heart sounds, cardiac output, cardiac wall motion, blood oxygen level, blood pH, heart rate variability, timing of myocardial impedance changes, and blood pressure.

18. The system of claim 15 wherein the stress index is computed as a function of one or more physiological variables selected from a group that includes a QRS width of an electrogram, QT interval of an electrogram, a time interval between electrically sensed contractions of different myocardial sites, a time interval between mechanically sensed contractions of different myocardial sites, the presence or absence of one or more particular heart sounds, cardiac output, cardiac wall motion, blood oxygen level, blood pH, heart rate variability, timing of myocardial impedance changes, and blood pressure.

19. The system of claim 15 wherein the external programmer is programmed to compute a separate parameter-specific protective index for adjusting each of a plurality of cardioprotection parameters in accordance therewith.

20. The system of claim 15 wherein the external programmer is programmed to map the deviation of the protective index from the desired protection level value to a plurality of cardioprotection parameters.

* * * * *